US011612757B1

(12) United States Patent
Comito et al.

(10) Patent No.: US 11,612,757 B1
(45) Date of Patent: Mar. 28, 2023

(54) INDUCEMENT, VERIFICATION AND OPTIMIZATION OF NEURAL ENTRAINMENT THROUGH BIOFEEDBACK, DATA ANALYSIS AND COMBINATIONS OF ADAPTABLE STIMULUS DELIVERY

(71) Applicant: Lifespan Extension Advocacy Foundation, Seaford, NY (US)

(72) Inventors: Keith Comito, Seaford, NY (US); Oliver Medvedik, Queens, NY (US); Ryan McGarry, Haymarket, VA (US)

(73) Assignee: Lifespan Extension Advocacy Foundation, Seaford, NY (US)

( * ) Notice: Subject to any disclaimer, the term of this patent is extended or adjusted under 35 U.S.C. 154(b) by 0 days.

(21) Appl. No.: 17/832,082

(22) Filed: Jun. 3, 2022

(51) Int. Cl.
| | |
|---|---|
| A61N 2/00 | (2006.01) |
| A61H 1/00 | (2006.01) |
| A61N 1/00 | (2006.01) |
| A61N 5/06 | (2006.01) |
| A61N 7/00 | (2006.01) |
| A61H 23/00 | (2006.01) |
| A61N 2/02 | (2006.01) |

(52) U.S. Cl.
CPC .............. *A61N 2/002* (2013.01); *A61H 1/00* (2013.01); *A61H 23/008* (2013.01); *A61N 2/006* (2013.01); *A61N 2/02* (2013.01); *A61N 5/0618* (2013.01); *A61N 7/00* (2013.01); *A61H 2201/10* (2013.01); *A61H 2201/102* (2013.01); *A61H 2201/1604* (2013.01); *A61H 2201/5005* (2013.01); *A61H 2201/5007* (2013.01); *A61H 2201/5092* (2013.01); *A61H 2205/02* (2013.01); *A61H 2230/105* (2013.01); *A61N 2005/0626* (2013.01); *A61N 2005/0647* (2013.01); *A61N 2005/0659* (2013.01); *A61N 2005/0661* (2013.01); *A61N 2005/0662* (2013.01); *A61N 2007/0026* (2013.01)

(58) Field of Classification Search
CPC ............ A61N 1/36132; A61N 1/36135; A61N 1/36139; A61N 1/3614; A61N 1/36146; A61N 1/36167; A61N 1/3615; A61N 1/36128; A61N 1/3605; A61N 1/18; A61N 1/36; A61N 2/002; A61N 2/004; A61N 2/006; A61N 2/02; A61N 2/06; A61N 2/12; A61N 2/00; A61B 5/4836; A61B 5/369; A61B 5/6803; A61B 5/24; A61B 5/398; A61B 5/163; A61B 5/4064; A61B 5/4848; A61B 5/0022; A61B 2018/00434; A61B 5/4088; A61B 5/378; A61B 5/4812; A61B 5/4076; A61B 5/168; A61B 2018/00642; A61B 5/38; A61B 5/375; A61B 5/165; A61B 5/486; A61B 5/291; A61B 3/0033; A61B 3/0041; A61B 3/0075; A61B 2018/00648; A61B 2018/00839
See application file for complete search history.

(56) References Cited

U.S. PATENT DOCUMENTS

2018/0133507 A1\* 5/2018 Malchano ............ A61N 5/0622

\* cited by examiner

*Primary Examiner* — Christine H Matthews
*Assistant Examiner* — Joshua Daryl D Lannu
(74) *Attorney, Agent, or Firm* — Cognition IP, P.C.; Edward Steakley; Schiller Hill

(57) ABSTRACT

Methods, systems and apparatus for inducing and verifying the level of neural entrainment at any target frequency, through a combination of biofeedback mechanisms, data analysis, and modulation of synergistic combinations of adaptable stimuli.

16 Claims, 11 Drawing Sheets

INDUCEMENT, VERIFICATION AND OPTIMIZATION OF NEURAL ENTRAINMENT THROUGH BIOFEEDBACK, DATA ANALYSIS AND COMBINATIONS OF ADAPTABLE STIMULUS DELIVERY

FIELD

The present invention relates generally to inducing and verifying levels of neural oscillatory entrainment in a host, through devices and methods which combine biofeedback mechanisms, data analysis, and modulation of synergistic combinations of adaptable stimuli.

BACKGROUND

Current methods to induce neural entrainment—for example stimulating cortical oscillations at various frequencies—most notably within the gamma range of 25 Hz-140 Hz—attempt to do so in a manner which relies on non-adaptive stimuli. An example would be the light stimuli flickering at an unchanging frequency, with the goal of achieving cortical oscillations at the same specific frequency, such as 40 Hz, which is also referred to as "gamma entrainment." Such systems may consist of either invasive or noninvasive stimuli, e.g. electrodes that are directly implanted within a cortical region for invasive stimulation or, more typically, noninvasive stimulation that is mediated through sensory neural stimulation. This can consist of either a single stimulus or combinations of stimuli that utilize light, sound or vibrations pulsed at specific frequencies, to stimulate retinal ganglion cells, auditory cells or motor neurons, respectively. Present systems lack the ability to alter the parameters of and/or combination of parameters of said stimuli, such as intensity, frequency, and combinations of stimulus modalities, as well as lack the feedback mechanisms which can measure neural entrainment and readjust stimulus parameters to optimally achieve a specified goal, such as maximal neural entrainment at a given frequency. These systems also lack the ability to record, store, and analyze data from multiple users in formats conducive to decentralized, participant led, clinical trials. Accordingly, such systems miss opportunities for said data to be used to further optimize individual protocols, determine which protocols are most effective for specific users or cohorts of users, e.g. users that have an age-related hearing or visual impairment [necessitating the presentation of stimuli in a different modality], are prodromal, have different levels of cognitive impairment, personality-cohesion disorders such as dissociative-identity-disorder, or are at various severities of dementia.

SUMMARY

The systems and methods described herein provide for the inducing and verifying of neural entrainment of a user. In some embodiments, the neural entrainment system may comprise a neural stimuli module and a verification module. The neural stimuli module may comprise one or more stimuli devices and one or more stimuli control modules.

In some embodiments, the neural stimuli module may be configured to set, by the stimuli control module, one or more operational parameters for the one or more stimuli devices, The stimuli control module may further control the operation of the one or more stimuli devices, wherein the operation of the one or more stimuli devices is based at least in part on the one or more operational parameters for the one or more stimuli devices. The one or more stimuli devices may then deliver one or more neural stimuli to the user.

In some embodiments, the verification module may further comprise one or more sensor modules, an electroencephalogram (EEG) module, other biofeedback modules and a data analysis module. In some embodiments some or all of the sensor models may be configured to detect/receive biological or physiological signals from a user (biological and physiological are used interchangeably and understood to be the same or similar in the scope of this disclosure.). The biological signals may be in signals generated response to the one or more stimuli, normally occurring biological/physiological signals and/or biological/physiological signals that have been altered/influenced as a result of the one or more neural stimuli being delivered to the user.

In some embodiments, the data analysis module may comprise a machine learning module, a cognitive assessment module, and a configuration module. The data analysis module may be configured to determine, by the cognitive assessment module, one or more efficacy values of a combination of the one or more neural stimuli. The efficacy values may be based at least in part on received user input and results from one or more clinical assessments.

In some embodiments, the machine learning module may determine if neural entrainment has been successfully achieved and/or an optimal level of entrainment has been achieved, based at least in part on the one or more biophysiological signals, the operational parameters of the one or more stimuli devices, and the determined efficacy values. If neural entrainment has not been successful, the level of entrainment achieved is below a threshold value, and/or the level of entrainment is not within a targeted value window, the machine learning module may be configured to determine one or more adjustments to the one or more operational parameters of the one or more stimuli devices.

In some embodiments, one or more stimuli profiles may be generated for each of the stimuli devices based on the analysis and determined adjustments, wherein the stimuli profiles comprises one or more operational parameters. The generated stimuli profiles may then be loaded into each of the stimuli devices by the stimuli control module. One or more neural stimuli may then be delivered to the user based on the generated stimuli profiles. The process of sensing, analyzing and adjusting may then be iterated until the system verifies that entrainment has successfully been achieved, entrainment has exceeded at least a lower threshold value, or entrainment within a window of values has been achieved.

The features and components of these embodiments will be described in further detail in the description which follows. Additional features and advantages will also be set forth in the description which follows, and in part will be implicit from the description, or may be learned by the practice of the embodiments. The detailed description and specific examples are intended for illustration only and are not intended to limit the scope of the disclosure.

BRIEF DESCRIPTION OF THE DRAWINGS

The present disclosure will become better understood from the detailed description and the drawings, wherein.

DETAILED DESCRIPTION

Figure 1:
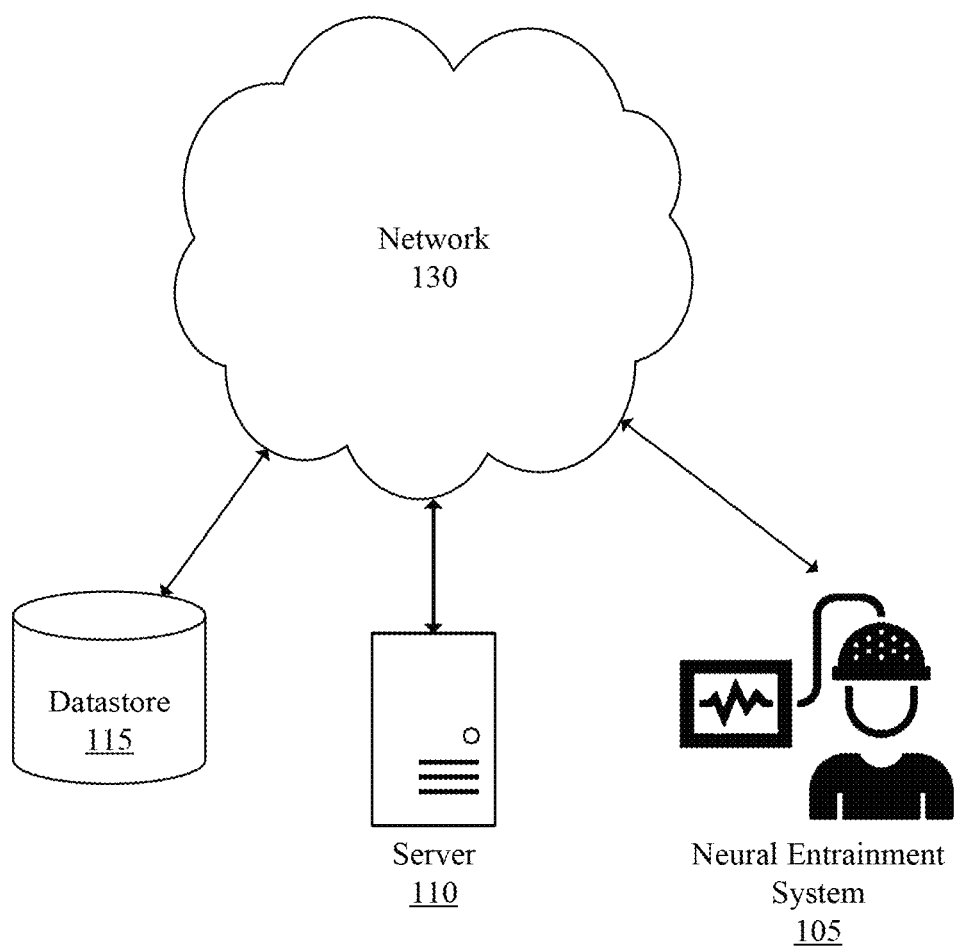
FIG. 1 is a diagram illustrating an exemplary neural entrainment platform in which some embodiments may operate.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

In addition, it should be understood that steps of the exemplary methods set forth in this exemplary patent can be performed in different orders than the order presented in this specification. Furthermore, some steps of the exemplary methods may be performed in parallel rather than being performed sequentially. Also, the steps of the exemplary methods may be performed in a network environment in which some steps are performed by different computers in the networked environment.

Some embodiments are implemented by a computer system. A computer system may include a processor, a memory, and a non-transitory computer-readable medium. The memory and non-transitory medium may store instructions for performing methods and steps described herein.

The following generally relates to a system and methods for inducing and verifying the level of neural entrainment at any target frequency, through a combination of biofeedback mechanisms, data analysis, and modulation of synergistic combinations of adaptable stimuli.

In some embodiments, the system may be configured to maximize the inducement of neural entrainment at specific frequencies in a human brain via a wearable device, which may independently and automatically modulate multiple entrainment-inducing stimuli (stimuli devices), based upon real-time biofeedback mechanisms. In some embodiments, real-time biofeedback mechanisms may include sensors for detecting heart rate (HR), finger temperature (FT), respiration rate (RR), linguistic analysis, voice frequency analysis, frequency/spectrogram analysis, carbon dioxide ($CO_2$), oxygen saturation ($SpO_2$). Sensors may also include galvanic skin resistance (GSR) sensors, pyroelectric sensors/thermometers, electrocardiograms (ECG), electromyograms (EMG), capnograms, EEG, eye tracking, retinal scanning, accelerometers, pressure sensors, inertial measurement units, gyroscopes and/or combination thereof. Other biofeedback mechanisms that are not in real-time can also be employed & contribute to the machine learning apparatus that has been described; e.g. up-regulated entrainment achieved through other means. The automatic modulation may be performed in an iterative manner in which the operating parameters of the stimuli devices are adjusted based on analysis of the real-time biofeedback from one or more sensors. This may allow for the automatic "zeroing in" on frequencies and stimuli parameters that are maximally effective for inducing such neural entrainment and consequent therapeutic effects on a per-user basis.

The system may be configured for rapid iterative testing of configurations and combinations, and optimization towards the maximal achievement of a desired effect, for example cortical neuronal entrainment, while allowing for flexibility and per-user variance in how that goal is maximally achieved. For example, in one user, maximal cortical entrainment could be achieved with a configuration profile of: entrainment frequency of 39 hz achieved via combination of 39 hz flickering blue light and 39 hz sine wave tone perfectly in phase with each other applied in 15-45 minute daily sessions, while in another user, maximal cortical entrainment could be achieved with a configuration profile of: entrainment frequency of 42 hz achieved via combination of 42 hz flickering green light and 1000 hz sawtooth wave tone pulsed at 42 hz in a square wave pulse pattern, with this sound wave at 30° phase delay relative to the light wave, applied in two 20 minute sessions per day.

The system may be configured to be equitably distributed in manners that is conducive to new models for crowd-sourced clinical trials. For example, the system may employ EEG-based feedback and/or machine learning algorithms to optimize cortical entrainment for individual users, as well as record and analyze data from multiple users, based on cognitive assessments and other assessments. This may allow for 1) determining the efficacy of various protocols in enhancing cognition and/or ameliorating dementia in the shortest time possible, 2) determining the minimal hardware components (such as number and type of EEG electrodes) necessary to attain sufficient biofeedback for such purposes as cost-effectively as possible, 3) guiding the development of future clinical trials, and 4) delivering to the user an optimized protocol for enhancing cognitive functions.

In some embodiments, the system may be configured for the acquisition of significant basic-research knowledge in the field of neuronal entrainment not hitherto known. For example, the system may allow the rapid testing of a wide spectrum of stimuli combinations to develop, for example, an atlas of neuronal entrainment propensity for the human brain, including metrics such as average time-to-peak-entrainment at frequency x, average maximum-power-spectrum-density-at-peak-entrainment at frequency x, etc. This in turn could lead to demonstrating that such propensities change in clearly quantifiable ways with parameters such as age or disease, thereby leading to the development of powerful biomarkers of brain age and/or disease presence.

This may also facilitate the acquisition of additional useful information which can be used to increase the efficacy of the system itself, such as the presence or absence of practice effects under varying scenarios, and metrics pertaining to the spatiotemporal propagation of entrainment throughout the brain in response to varying stimuli and scenarios.

The system may also be configured to facilitate the acquisition of basic research knowledge in additional areas beyond the strictly medical, such as the study of consciousness. For example, a demonstration of significant neuronal entrainment as a result of a unique combination of stimuli not reported as consciously perceived, such as infrared light and ultrasound, may yield new information regarding the neural correlates of conscious experience, increase understanding of comas and anesthesia, and suggest useful follow-up experiments.

An additional manner in which basic research would be conducted is through the examination of tangential effects of entrainment protocols. For instance, it is common that sensory perception and responses can decline after repeated exposure to certain stimuli (e.g. the beeping sound that car safety systems emit when the seatbelt is not attached, which can cause an individual to eventually tune this out if the sound is not altered in some way). Therefore, this system can be used to conduct basic research on the effects of entrainment protocols, and adjust the parameters in cases where entrainment effects decline.

In some embodiments, the system may be used as a diagnostic, prognostic and therapeutic device. Biofeedback from the system may be used to diagnose one or more cognitive or neurological disorders. Diagnosis and prognosis may be based on the time to entrainment, ease of entrainment, response to entrainment stimulation measured in the maximum level of entrainment that can be achieved, or one or more stimuli response profiles or combination thereof.

In some embodiments, when maximal entrainment does not directly correlate to maximal therapeutic effectiveness, the system may be configured to modify the entrainment profile until a maximal entrainment is reached. From the maximal entrainment profile, the system may adjust and tune the profile to reach the optimal window of entrainment. Within the optimal window of entrainment there may be differing levels of therapeutic effectiveness for the user. These levels may be unique to each individual user. In some embodiments, one or more machine learning models may be configured to determine one or more optimal windows of entrainment levels. Over time, the optimal windows may evolve based on the analysis of data from diagnosed and undiagnosed users.

In some embodiments, the system may be configured to identify one or more stimuli profiles for each of a plurality of cognitive and neurological conditions. Cognitive and neurological conditions may include Alzheimer's, Parkinson's, Multiple Sclerosis, Covid, long-haul Covid, depression, sleep disorders, ADHD, personality cohesion disorders, Epilepsy and other seizure disorders. In some embodiments functional connectivity FD values may be used as a metric corresponding to the severity of Alzheimer's Disease in a patient. The stimuli profiles may be optimized with regard to a therapeutic effectiveness value. The therapeutic effectiveness value may be normalized and/or weighted. The system may determine a therapeutic effectiveness value for a condition being treated based on analysis of a user's entrainment session data (stimuli profile, stimuli response profile, time to entrainment, ease of entrainment, biofeedback information, etc.) and one or more cognitive tests taken by the user. For each cognitive and neurological condition, one or more diagnostic machine learning models may be trained on anonymized entrainment session data from users previously treated for said condition. The training of models for each condition may also include entrainment session data from healthy or undiagnosed users being exposed to predetermined stimulus protocols for treating underlying conditions. Users undergoing diagnosis may be subjected to entrainment protocols and stimuli profiles in an entrainment session for a plurality of conditions. The diagnostic machine learning models for corresponding conditions may then analyze the entrainment session data and determine a condition diagnosis likelihood for the user. Furthermore, the diagnosis criteria may be based on resting-state based functional connectivity/FD values measured using the EEG device. There has been extensive literature demonstrating that FD values have been used to classify dementia states in patients, which is the same technique that our technology will apply for diagnosis.

In some embodiments, certain conditions, such as seizure and epilepsy may be mitigated by decreasing neural entrainment at a certain frequency (the one at which the neurons may be having an out of control positive feedback loop). For example, if entrainment at frequency X can decrease entrainment at frequency Y (via, for example, destructive interference), the system may be configured to maximize entrainment at frequency X to reduce the negative impact of entrainment at frequency Y. For certain conditions, therapeutic effectiveness may be tied to decreasing entrainment at frequency Y via stimuli to increase of entrainment at frequency X.

In some embodiments, stimuli devices may be configured to deliver non-invasive and/or non-pharmacological neural stimuli that can be varied in amplitude, frequency and/or shape. The stimuli may be either single stimuli or combinations of multiple stimuli that utilize light, sound or vibrations pulsed at specific frequencies, to stimulate retinal ganglion cells, auditory cells or motor neurons, respectively. Each of the stimuli may be precisely controllable, and with the relationships between each precisely known.

In some embodiments the system may be configured as a headset, worn by the user, or configured into an item of furniture, such as a chair, chaise lounge, bed, etc. or as physically separated components that can interact as in the internet of things (IOT). In some embodiments, separated components may include LED light strips, audio speakers, haptic devices, ultrasonic transducers, infrasound speakers or combination thereof. In some embodiments, the stimuli may be based on, but are not limited to, light, sound, infrared light, ultraviolet light, infrasound, ultrasound, physical vibrations, transcranial direct and alternating current stimulation (tDCS/tACS), transcranial magnetic stimulation (TMS) and aromas.

In some embodiments, the system may contain an EEG or similar system for measuring and recording the electrical activity of the cortex in response to the stimuli.

FIG. 1 is a diagram illustrating an exemplary neural entrainment platform 100 in which some embodiments may operate. The neural entrainment platform 100 may comprise a neural entrainment system 105, one or more servers 110, one or more datastores 115 and one or more networks 130.

The neural entrainment system 105 may be any computing device capable of communicating over network 130. A neural entrainment system 105 may be integrated into a notebook computer, smartphone, personal digital assistant, desktop computer, tablet computer, furniture, head mounted displays, wearable computing devices, smartwatches, EEG units or other computing device.

The neural entrainment system 105 may comprise an EEG or similar system for measuring and recording the electrical activity of the cortex in response to the stimuli. In some embodiments, the neural entrainment system may be configured to manage the duration, amplitude, frequencies, color, volume, pitch, waveform shape, etc. of the various stimuli produced by the stimuli devices. In some embodiments, the neural entrainment system 105 may control the stimuli device to produce a stimuli with diminishing wave amplitudes, different patterns and sequences of stimuli, different patterns and sequences of periods of no stimuli during entrainment, random stimulation at regular intervals, random stimulation when certain EEG patterns are detected, triggering a stimuli protocol/profile when acute symptoms of a disease are detected (tremors, seizures) or combination thereof.

The neural entrainment system 105 may further be configured to verify proper configuration of physical positioning and operation of hardware and control modules. In some embodiments, adjustment/repositioning directions may be provided to the user when the physical positioning of the hardware on the user is incorrect. For example, machine learning algorithms may be applied to EEG data and camera data during setup to verify the proper configuration and placement of wearable device(s).

The neural entrainment system 105, may also be configured to integrate/aggregate inputs obtained from the EEG and/or other biofeedback systems, the output of which can inform the duration, frequency and amplitudes, etc. of the various stimuli, in order to optimize the entrainment of cortical neuron firing to a desired entrainment frequency, e.g. 40 Hz gamma entrainment.

In some embodiments the system may perform and record cognitive assessments from users, as administered on a digital device, such as a tablet, laptop, smartphone, wearable electronic device, etc. In some embodiments the system may record and analyze the data from all or part of the above processes for the purposes of administering a participant-led trial. An example of such a trial would be to assess the efficacy of various stimuli and other protocol variables to alter and/or improve cognitive functions, either to enhance normal cognitive functions or to treat a cognitive disorder, e.g. a dementia related disease such as Alzheimer' Disease.

Server 110 may be one or more physical or virtual machines configured to communicate with the one or more neural entrainment systems 105 and datastores 115. The one or more servers may be configured as a distributed computing infrastructure and processing of applications and other software may be carried out on the cloud.

Datastores 115 may communicate with one another over network 130. Datastores 115 may be any storage device capable of storing data for processing or as a result of processing information at the neural entrainment system 105 and/or servers 110. The datastores 115 may be a separate device or the same device as server 110. The datastore 115 may be located in the same location as that of server 110, or at separate locations.

Network 130 may be an intranet, internet, mesh, LTE, GSM, peer-to-peer or other communication network that allows the one or more servers 110 to communicate with the one or more neural entrainment system 105 and datastores 115.

Figure 2A:
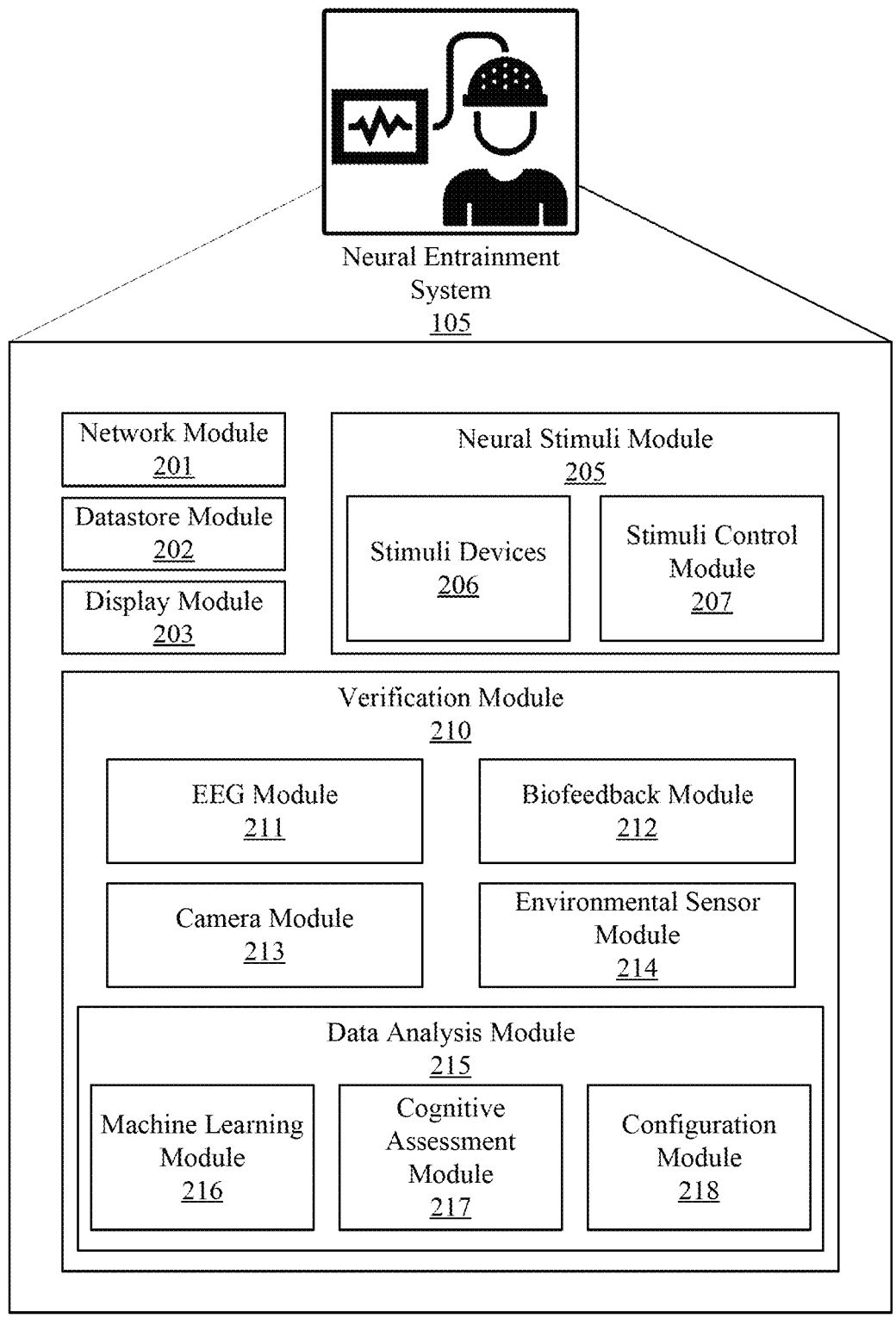
FIG. 2A is a diagram illustrating an exemplary neural entrainment system in accordance with aspects of the present disclosure.

FIG. 2A is a diagram illustrating an exemplary neural entrainment system 105 in accordance with aspects of the present disclosure. Neural entrainment system 105 may comprise network module 201, datastore module 202, display module 203, one or more neural stimuli modules 205 and one or more verification modules 210. Network module 201 may transmit and receive data from other computing systems via a network. In some embodiments, the network module 201 may enable transmitting and receiving data from the Internet. Data received by the network module 201 may be used by the other modules. The modules may transmit data through the network module 201.

The datastore module 202 may be configured to store operation data such as logs and configurations of the system and its components. Datastore module 202 may also be used to store datasets. The datasets may be generated within the neural entrainment system 105, or retrieved from an external source, such as database 115. The machine learning module 216 may use datasets in the datastore 202 to train one or more machine learning models.

Display module 203 may be any device configured to display graphical representations of information (LCD display, OLED display, DLP display, etc.).

The one or more neural stimuli modules 205 may further comprise stimuli devices 206 and stimuli control module 207. Stimuli devices 206 may be configured to deliver non-invasive and/or non-pharmacological neural stimuli that can be varied in amplitude, frequency and/or shape. The stimuli may be either single stimuli or combinations of multiple stimuli that utilize light, sound or vibrations pulsed at specific frequencies, to stimulate retinal ganglion cells, auditory cells or motor neurons, respectively. In some embodiments, dimming mechanisms may be used instead of generating mechanisms regarding any stimulus. For example, instead of flickering a light on and off at 40 hz, a similar stimulus can be the periodic shuttering off of visual stimuli, such as a television screen or an image on a computer monitor or cell phone. Hence in some embodiments, such stimuli hardware components may be integrated into non-obvious platforms, such as video streaming services.

In some embodiments, the system may be configured to employ variable and tunable inputs in combination, tunable target entrainment frequency, along with biofeedback systems which can verify the results in real time and, accordingly, inform adjustment of the inputs and/or target entrainment frequencies, by either manual or automatic processes. The system may employ combinations of tunable stimuli, providing the ability to work around user-specific issues such as epilepsy (by disqualifying certain light selections), age-related hearing or vision loss (e.g. pulsing a desired frequency at a carrier frequency the user is able to hear) and lack of focus/tiredness (by varying the stimuli in an engaging manner).

In some embodiments, the system may be configured to employ a machine learning model to automatically detect and reject noisy segments of biofeedback data such as EEG, enabling faster analysis and more accurate detection of neural entrainment.

The system may provide a more precise understanding as to the efficacy of combinations of neural stimuli and precise causality of any such determined efficacy through the incorporation of real-time biofeedback and tunability of all input and output parameters. For example, consider a proposed therapy consisting of 40 Hz light stimulation to remediate Alzheimer's Disease. If this is failing in a particular subject, as ascertained through a variety of clinical assessments such as cognitive assessment tests, PET scans, MRI scans, etc., the system will provide an indication that the stimulatory intervention has failed at the first step, not achieving sufficient 40 hz entrainment, or has failed at the second step, 40

Hz entrainment has been achieved but has not resulted in an efficacious treatment of Alzheimer's Disease.

In some embodiments, additional add-on interventions not physically connected to the system, such as the effect of different aromas, mediation, binaural sound, and music, for example, may be incorporated into the analysis of whether individually or in combination they can also ameliorate cognitive deficits or enhance normal cognitive functions. The system thus may be used to determine if such additional interventions have an additive or synergistic effect in combination with any other stimuli, including the ones already mentioned. This may allow the system to be used as a detector of other potential therapies or adjuvants.

Each of the stimuli may be precisely controllable, and with the relationships between each precisely known. In some embodiments wave-based stimuli can be varied in amplitude, carrier wave frequency and shape, pulse wave frequency and shape, duty cycle, etc., such that each stimuli may be precisely controllable, and with the relationships between each stimuli precisely known and controllable—for example, the wave phase delay offset between light and sound stimuli.

Stimuli control module 207 may be configured to manage operational parameters of the one or more stimuli devices 206. The stimuli control module 207 may receive, store, generate and/or modify stimuli profiles for the one or more stimuli devices. The stimuli control module 207 may also initiate the operation of each of the stimuli devices based on one or more stimuli profiles associated with the stimuli device. In some embodiments, there may be combinational stimuli profiles which are configured to operate a plurality of stimuli devices in a precise relationship to one another.

The one or more verification modules 210 may comprise EEG module 211, biofeedback module 212, camera module 213, one or more environmental sensor modules 214 and data analysis module 215. EEG module 211 may be any head mounted device with one or more contacts, leads or sensors configured to detect brain activity. Biofeedback module 212 may be any sensor which collects biological/physiological data from a user. For example, the biofeedback module 212 may comprise sensors for detecting heart rate (HR), finger temperature (FT), respiration rate (RR), linguistic analysis, voice frequency analysis, frequency/spectrogram analysis, carbon dioxide ($CO_2$), oxygen saturation ($SpO_2$). Sensors may also include galvanic skin resistance (GSR) sensors, pyroelectric sensors/thermometers, electrocardiograms (ECG), electromyogram (EMG), accelerometers, pressure sensors, inertial measurement units, gyroscopes and/or combination thereof.

Camera module 213 may be any sensor configured to capture images of an environment. For example, the camera module 213 may be configured to capture images in the visible light range, ultraviolet range or infrared range. In some embodiments, the camera module 213 may be a depth sensing camera or a sensor configured to generate a point cloud model such as LIDAR.

One or more environmental sensor modules 214 may comprise one or more sensors configured to measure conditions in proximity to neural entrainment system 105. In some embodiments, the one or more environmental sensor modules 214 may be configured to identify and measure environmental noise and interference. Environmental sensor modules 214 may also be configured to collect information related to location, altitude, magnetic flux, acceleration, orientation, temperature altitude or combination thereof. In some embodiments, adjustments to the stimuli may be made based on the conditions sensed. For example, if a user is in a room that is overly saturated with red light, a visual stimuli may be changed from red to green to distinguish the stimuli from the ambient light present in the room. In some embodiments, electrical interference and noise may be detected by one or more environmental sensors 214. For example, electrical interference and noise in the environment may adversely affect entrainment when the stimuli operates at the same or similar frequencies to that of the interference. The system may adjust the frequency of the stimuli or characteristics of the stimuli to reduce the interference and maximize the efficacy of the entrainment.

The data analysis module 215 may further comprise machine learning module 216, cognitive assessment module 217, configuration module 218. The data analysis module 215 may be configured to receive and aggregate sensor data and information collected from the EEG module 211, biofeedback module 212, camera module 213, environmental sensor module 214 and/or any other biological/physiological sensor connected or integrated into the system. The received and aggregated data may be analyzed by the machine learning module 216 to determine if the entrainment was a success/failure, if a level of therapeutic effectiveness was reached, one or more therapeutically effective windows of entrainment values or if the entrainment level achieved is within a therapeutically effective window. The level of success may be defined by the greatest power value achieved in response to Gamma stimulation. The machine learning module 215 may also be configured to detect and filter noise in the sensor readings. The machine learning module 215 may also be configured to predict entrainment levels based on the current stimuli profiles, sensor readings and determined or proposed adjustments to the stimuli profiles.

In some embodiments, data analysis module 215 may be configured to determine a therapeutic effectiveness value of the current intervention. The data analysis module 215 may be configured to prioritize therapeutic effectiveness over entrainment level. In some embodiments, the aggregated data may be analyzed to identify an entrainment value window, within which therapeutic effectiveness is maximized. In some embodiments, a stimuli profile that produces maximal entrainment may not provide the most therapeutic benefit to the user. For example, too much entrainment may potentially cause discomfort or agitation in some users and result in the effectiveness of the session being disrupted.

Cognitive assessment module 217 may be configured to receive or perform one or more clinical assessments, such as cognitive assessment tests, PET scans, MRI scans, and/or user input.

Configuration module 218 may be configured to generate stimuli profiles and/or combination of stimuli profiles to be used by the stimuli control module 207. Combinational sets of stimuli profiles may be generated by the configuration module 218 to be run in sequence by the stimuli control module 207. The combinational sets may also be run out of sequence or at random.

Figure 2B:
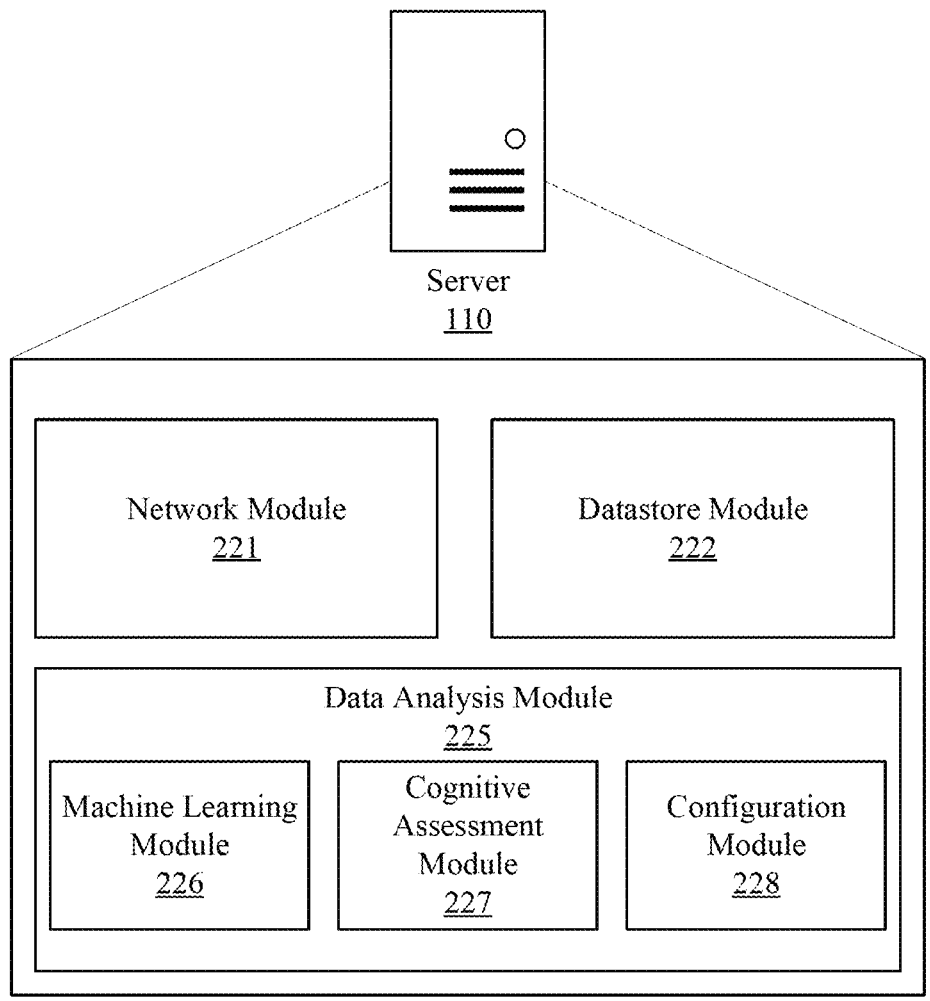
FIG. 2B is a diagram illustrating an exemplary server in accordance with aspects of the present disclosure.

FIG. 2B is a diagram illustrating an exemplary server 110 in accordance with aspects of the present disclosure. Server 110 may comprise network module 221, datastore module 222 and data analysis module 225.

Network module 221 and datastore module 222 may be the same or similar to that of network module 201 and datastore module 202 in FIG. 2A. Data analysis module 225, machine learning module 226, cognitive assessment module 227 and configuration module 228 may be the same or similar to that of data analysis module 215, machine learning module 216, cognitive assessment module 217 and configuration module 218 in FIG. 2A.

Figure 3A:
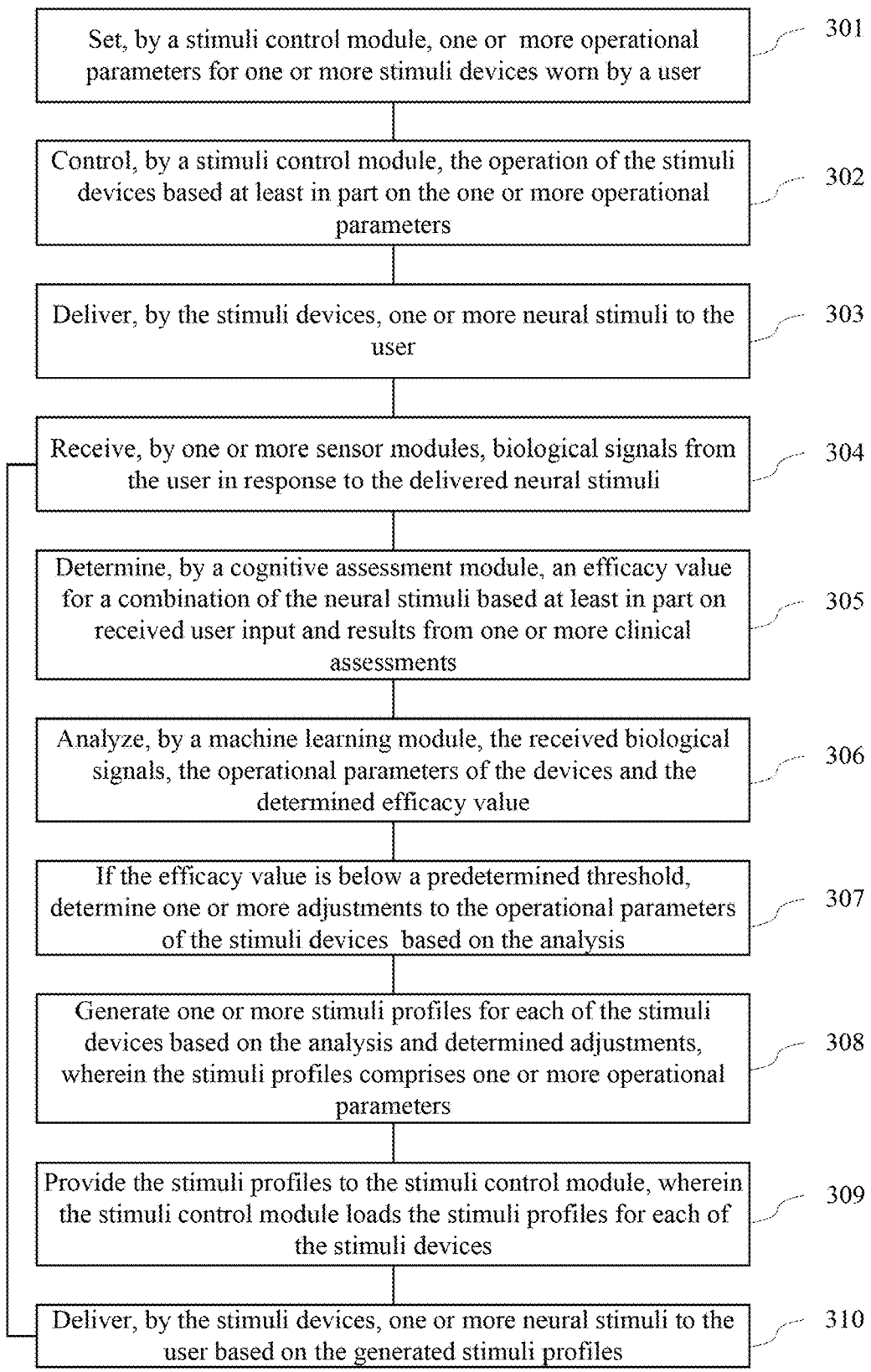
FIG. 3A is a flow chart illustrating an exemplary method that may be performed in accordance with some embodiments.

FIG. 3A is a flow chart illustrating an exemplary method 300 that may be performed in accordance with some embodiments.

At step 301, the system is configured to set, by a stimuli control module, one or more operational parameters for one or more stimuli devices worn by a user.

At step 302, the system is configured to control, by a stimuli control module, the operation of the stimuli devices based at least in part on the one or more operational parameters.

At step 303, the system is configured to deliver, by the stimuli devices, one or more neural stimuli to the user.

At step 304, the system is configured to receive, by one or more sensor modules, biological signals from the user in response to the delivered neural stimuli.

At step 305, the system is configured to determine, by a cognitive assessment module, one or more efficacy values for a combination of the neural stimuli based at least in part on received user input and results from one or more clinical assessments.

At step 306, the system is configured to analyze, by a machine learning module, the received biological signals, the operational parameters of the devices and the determined efficacy values.

At step 307, the system is configured to determine if one or more of the efficacy values are below a predetermined threshold value. If one or more of the efficacy values are above the predetermined threshold value and/or within a therapeutically effective window of values, a stimuli profile, containing the configuration of the stimuli devices, efficacy values, sensor data and other representative data, may be stored and labeled/classified as a therapeutically effective neural entrainment session. Different levels of therapeutic effectiveness may be determined and stored for each session. Comparison of the therapeutic effectiveness between sessions may be used to choose an optimal stimuli profile to use in future entrainment sessions. In some embodiments, comparison of the labeled and classified entrainment sessions may be used to predict the effects of adjustments made to the stimuli profile. The predictions may then be used in the selection and creation of a new stimuli profile that will be used in a future session. In some embodiments, an aggregated efficacy value (therapeutic effectiveness value) may be used to determine success/failure of an entrainment session. The therapeutic efficacy value may be related to a window of entrainment values. There may be multiple levels of successful neural entrainment that correspond to a successful entrainment session and a maximization of an aggregate efficacy value. The multiple levels may fall within a window of entrainment values. The window may be modified and shrunken at each iteration to further optimize the efficacy of the current intervention/treatment (stimuli profile). In some embodiments, there may be a continuous spectrum of successful neural entrainment, wherein the spectrum begins at the predetermined threshold and ends at a target goal value. The predetermined threshold and target goal value may be set manually or determined by the system before the optimization process starts. The threshold and the target goal value may be modified and adjusted during the optimization process based on sensor readings, additional training data, user demographics, user specific information or combination thereof. In some embodiments, if a predetermined number of efficacy values are below the predetermined threshold value, a stimuli profile labeled/classified as a failure to induce neural entrainment may be stored. In some embodiments, neural entrainment failure may be based on the magnitude of the difference between one or more efficacy values and one or more predetermined thresholds, an aggregate magnitude of differences between the efficacy values and the predetermined thresholds or an aggregate threshold, the magnitude of the differences of the values below the predetermined thresholds or an aggregate threshold. The aggregate threshold may be determined based on the predetermined threshold values corresponding to efficacy values included in the determining of success or failure of the neural entrainment. For example, if a failure is being determined based on a plurality of efficacy values that are below their corresponding predetermined thresholds, an aggregate threshold may be determined based on the predetermined thresholds corresponding to the failed efficacy values. The system may then determine one or more adjustments to the operational parameters of the stimuli devices based on the analysis.

At step 308, the system is configured to generate one or more stimuli profiles for each of the stimuli devices based on the analysis and determined adjustments.

At step 309, the system is configured to provide the stimuli profiles to the stimuli control module, wherein the stimuli control module loads the stimuli profiles for each of the stimuli devices.

At step 310, the system is configured to deliver, by the stimuli devices, one or more neural stimuli to the user based on the generated stimuli profiles. The process then returns to step 304, wherein the process of receiving and analyzing the biological signals is repeated until a successful neural entrainment is identified/verified.

Figure 3B:
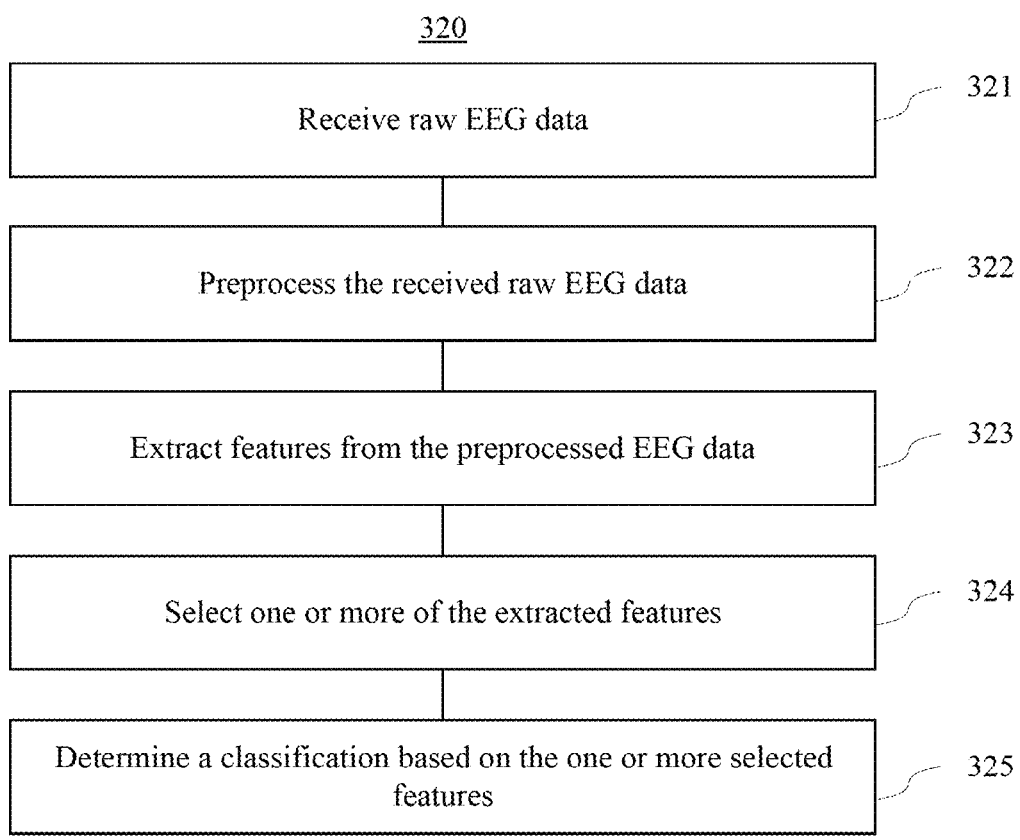
FIG. 3B is a flow chart illustrating an exemplary method that may be performed in accordance with some embodiments.

FIG. 3B is a flow chart illustrating an exemplary method 320 that may be performed in accordance with some embodiments.

At step 321, the system is configured to receive raw EEG data.

At step 322, the system is configured to preprocess the received raw EEG data. In some embodiments, the preprocessing may be configured to isolate the detected brain signals from internal (electrical impulses from muscle movement) and external (power lines and electronics) sources of noise. The preprocessing may also include re-referencing the channels to the average signal, running a Butterworth band-pass filter (1-57 Hz), and running a frequency decomposition to separate the data into power bands.

At step 323, the system is configured to extract features from the preprocessed EEG data. In some embodiments, independent component analysis (ICA) may be used to extract features from the preprocessed EEG data. Along with ICA, a supervised machine learning model may be used to label the sources of interference (e.g. power line, ocular, cardiac, muscle, etc.).

At step 324, the system is configured to select one or more of the extracted features. The machine learning model may also be used to identify Gamma activity/entrainment features from the preprocessed EEG data. The isolated and clear plots of Gamma activity/entrainment may then be selected for classification.

At step 325, the system is configured to determine a classification based on the one or more selected features. In some embodiments, the machine learning model may be used to identify whether entrainment is successfully taking place by providing a binary output (Gamma activity or no Gamma activity), a level of therapeutic effectiveness of the entrainment or if entrainment is achieved within a window of entrainment values that correlate to a therapeutically effective session.

Figure 4A:
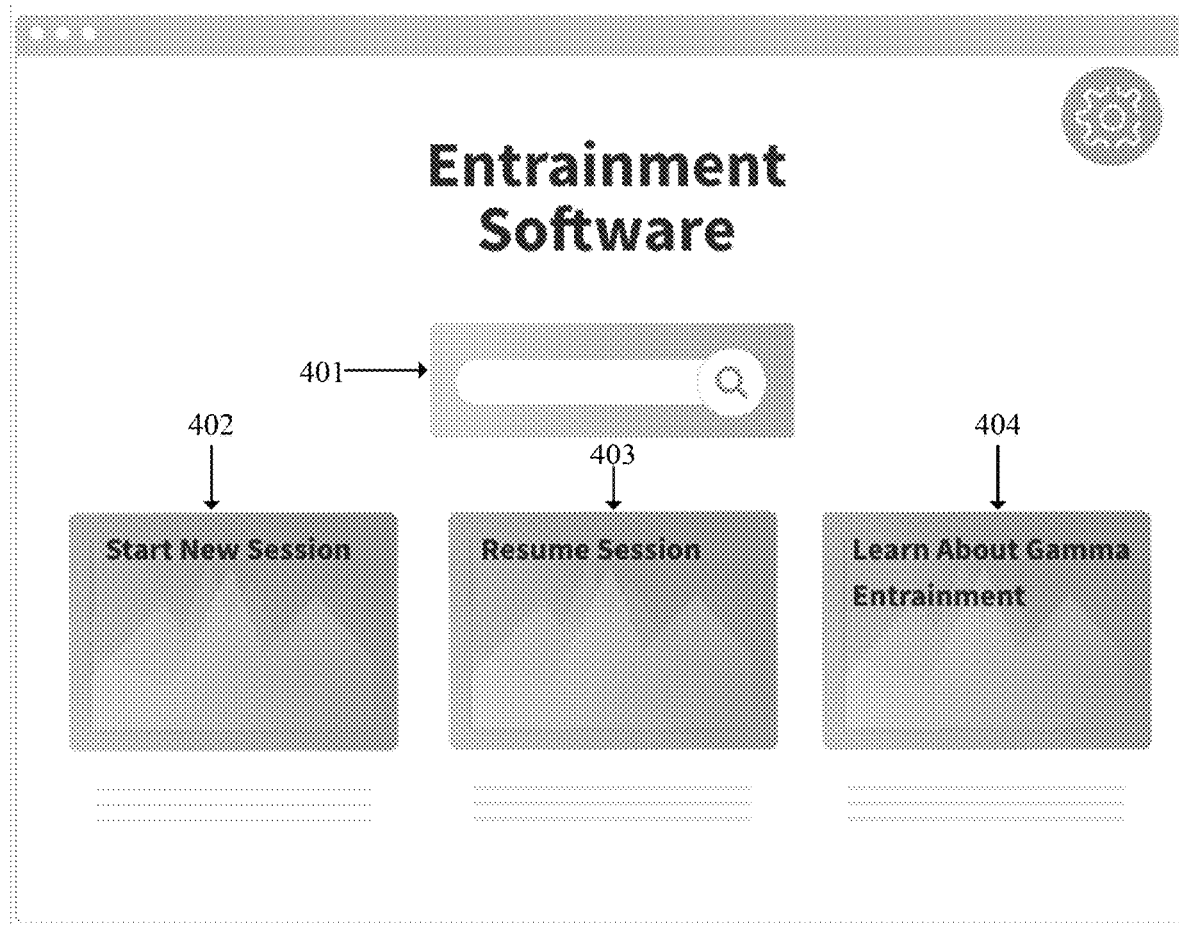
FIG. 4A is an exemplary user interface in accordance with aspects of the present disclosure.

FIG. 4A is an exemplary neural entrainment user interface (UI) 400 in accordance with aspects of the present disclosure. Neural entrainment UI 400 may comprise a search field 401 configured to provide a user with functionality to search through past entrainment sessions, new session button 402 for creating a new session, resume session button 403 to resume a session already in progress and an information button 404 which may be configured to provide information on the entrainment process or information related to a specific entrainment treatment protocol.

Figure 4B:
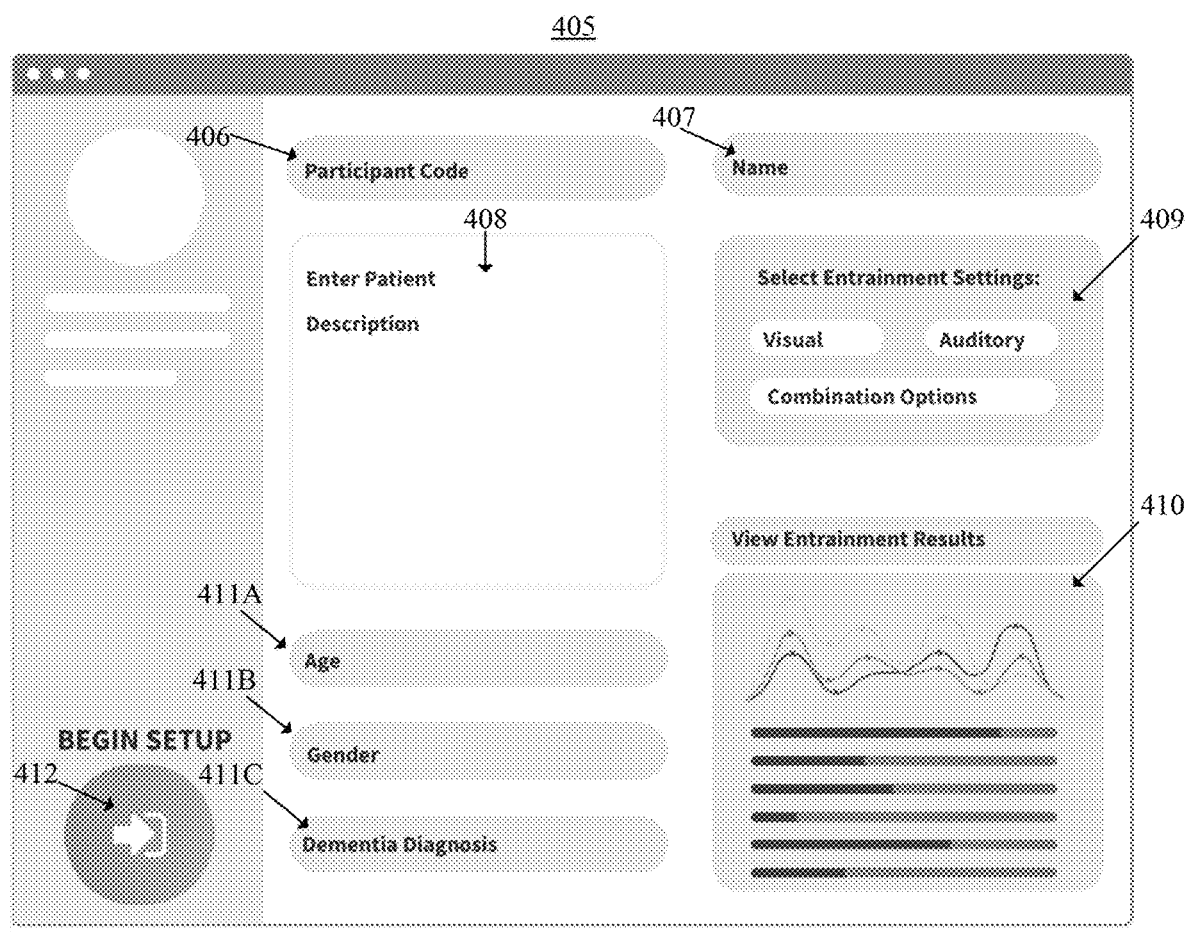
FIG. 4B is an exemplary user interface in accordance with aspects of the present disclosure.

FIG. 4B is an exemplary user profile UI 405 in accordance with aspects of the present disclosure. The user profile UI 405 may comprise user information. A participant code may be used to uniquely identify the user. In some embodiments, the participant code may be associated with a blockchain-based non-fungible token (NFT), or a wallet ID on a decentralized ledger, which can facilitate privacy, clearly permission-ed data access and/or accrual of cryptocurrency rewards for utilizing the system and/or contributing data.

The UI may display a patient name 407 and a patient description 408, along with one or more entrainment settings 409 and patient entrainment results 410. In some embodiments, patient demographic information 411A-411C stored and displayed within the UI 405. The user may be provided with a setup button 412 to begin an entrainment system setup process. Some or all of the information fields may be editable.

Figure 4C:
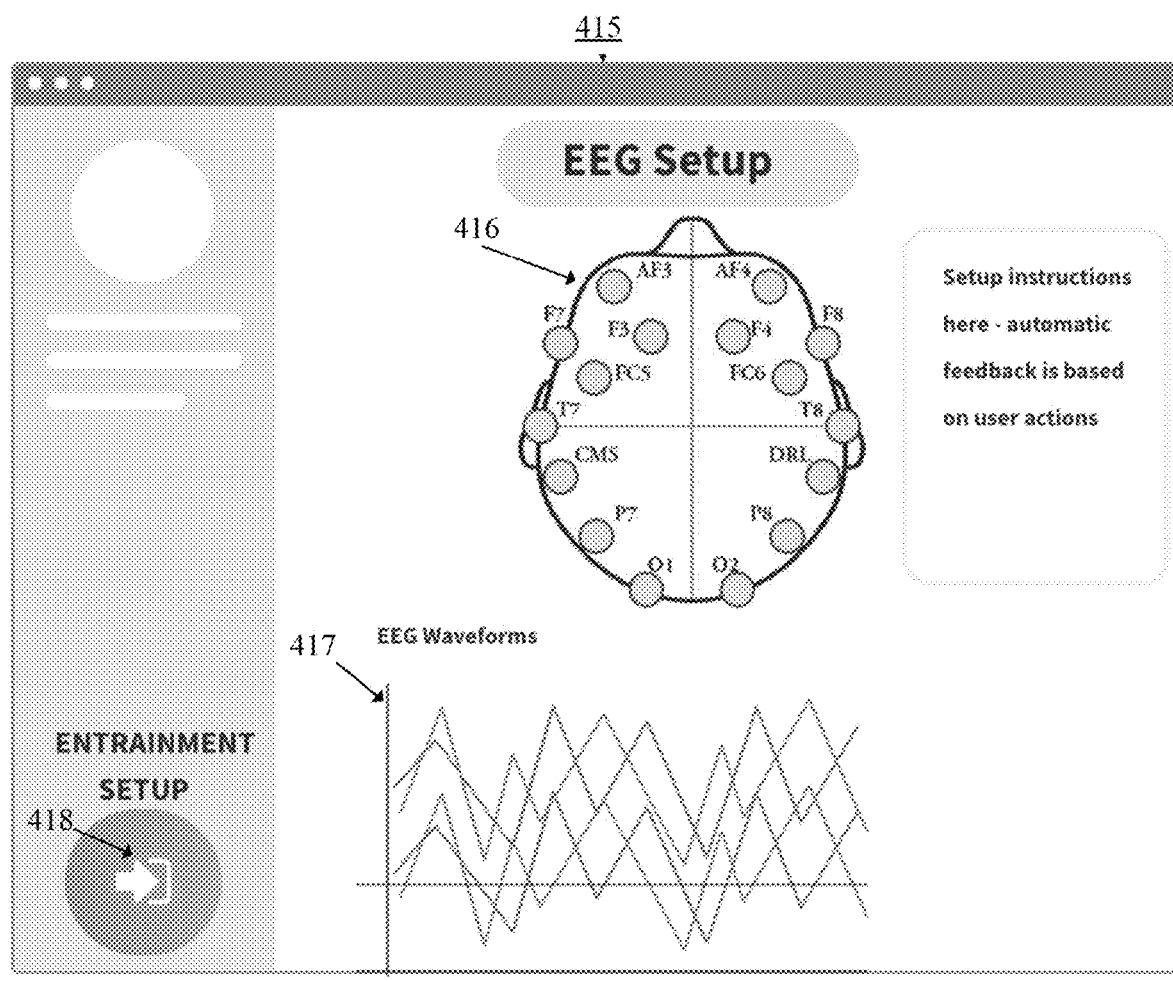
FIG. 4C is an exemplary user interface in accordance with aspects of the present disclosure.

FIG. 4C is an exemplary EEG setup UI 415 in accordance with aspects of the present disclosure. EEG setup UI 415 may comprise EEG lead information 416, EEG waveform graph 417 and an entrainment setup button 418. EEG information 416 may be configured to display positioning of one or more leads upon the user's head, and information related to the function of each lead. The individual lead indicators (circles) may be animated in a manner to convey visualization of the functioning of the lead and the data gathered or generated. The lead indicators may visually represent one or more analytical results. EEG waveform graph 417 may display one or more waveforms received from the one or more EEG leads. The waveforms may be raw or processed. The user may proceed through the setup by selecting the entrainment setup button 418.

Figure 4D:
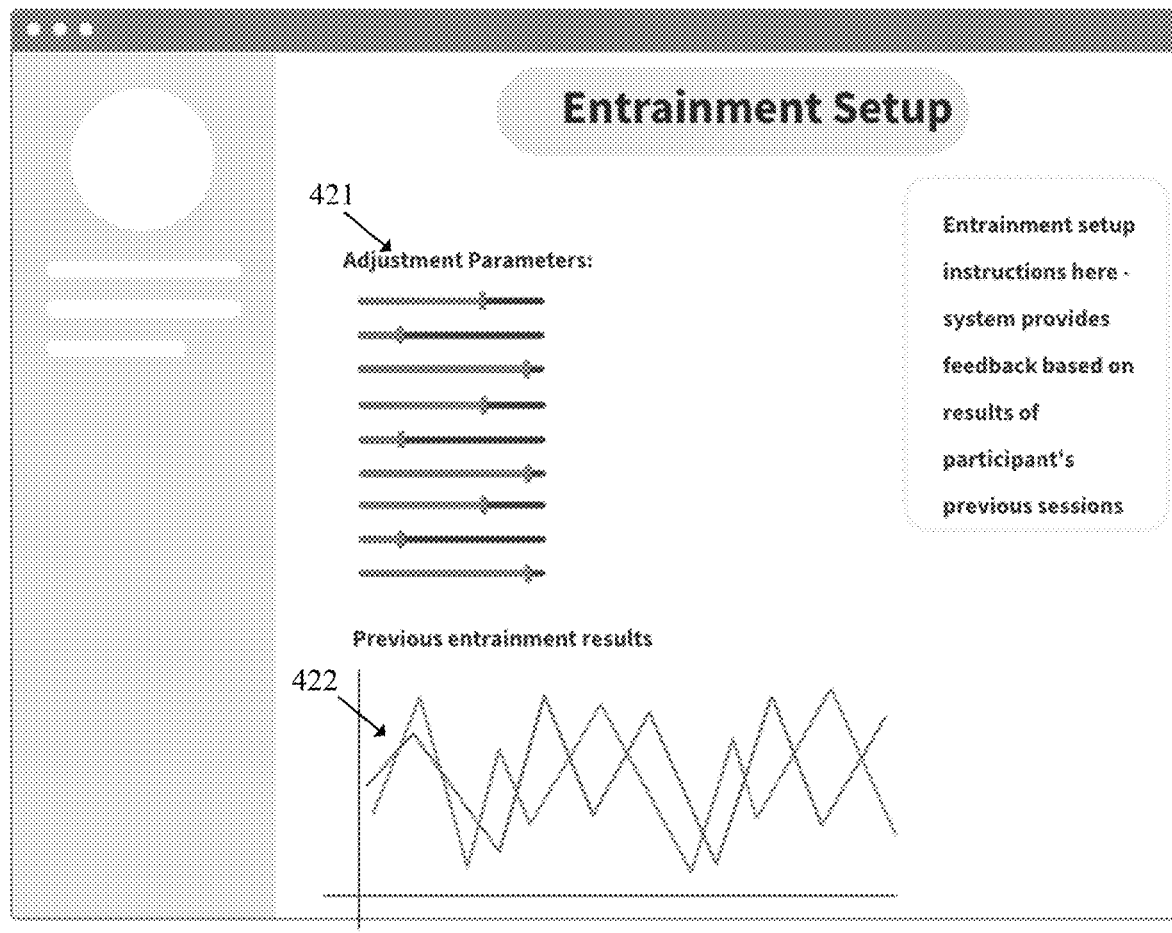
FIG. 4D is an exemplary user interface in accordance with aspects of the present disclosure.

FIG. 4D is an exemplary entrainment setup UI 420 in accordance with aspects of the present disclosure. Entrainment setup UI 420 may comprise a parameter setting section 421 a historic entrainment results graph 422. The parameter setting section 421 may comprise a one or more adjustable parameters and may include a visual indication of the deviation of a parameters current value from a default or recommended value.

Figure 4E:
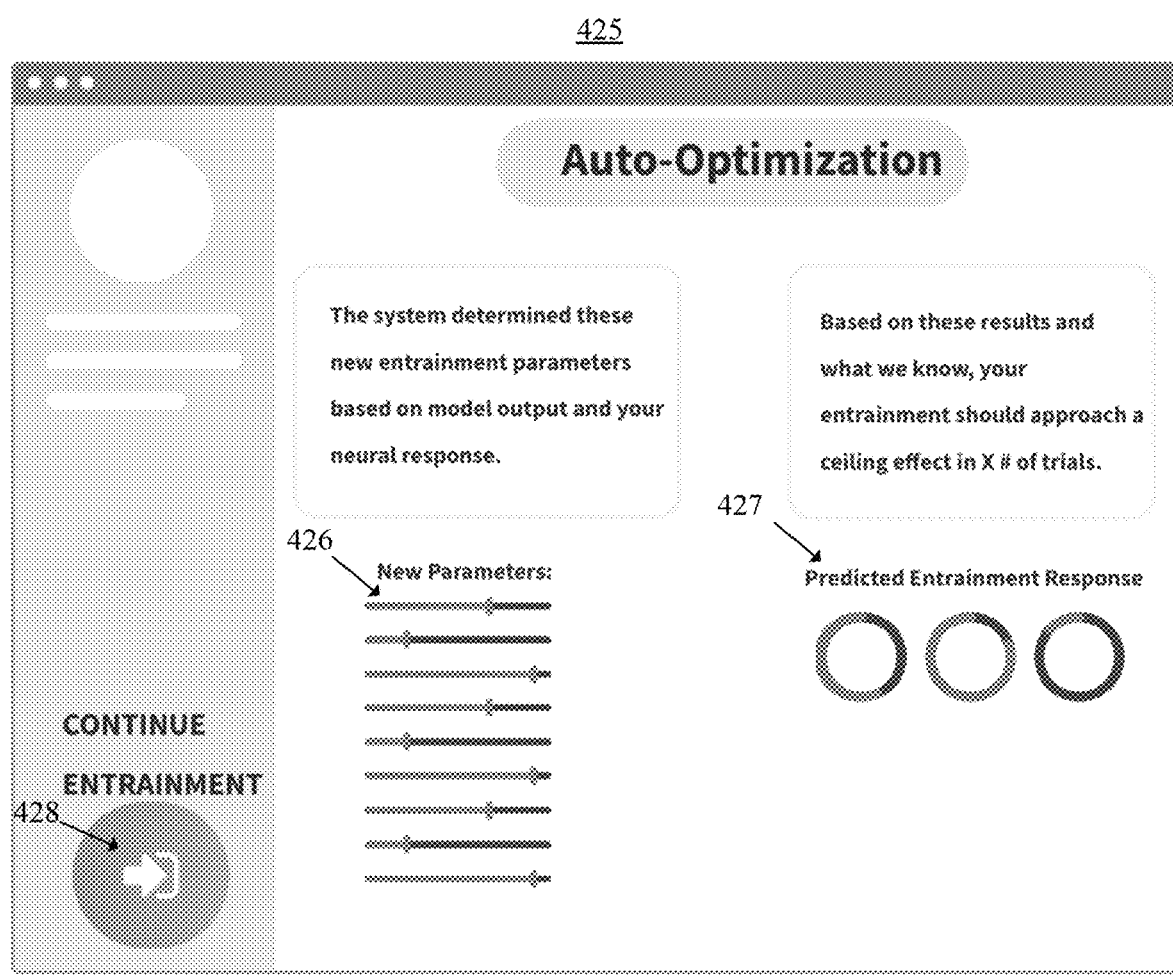
FIG. 4E is an exemplary user interface in accordance with aspects of the present disclosure.

FIG. 4E is an exemplary auto-optimization UI 425 in accordance with aspects of the present disclosure. Auto-optimization UI 425 may be configured to display a new parameters section 426, a predicted entrainment response section 427 and a continue button 428. During or after a session, the system may perform an analysis of current or historic entrainment session data. One or more machine learning models may be used to evaluate the efficacy of the past and current neural entrainment sessions and generate a parameter set, updated with new parameter values.

In some embodiments, local machine learning models may be used to protect personally identifiable information (PII). Information that cannot be processed or analyzed locally may be stripped of PII before sending the data to machine learning modules operating remotely, such as models running on cloud platforms.

In some embodiments, the refinement of knowledge and auto-optimizations described here may be based on continual refinements and learnings of the entire system across all participants on top of the user data collected locally.

Predicted entrainment response section 427 may be configured to display an expected result in relation to the new parameter value. In some embodiments, the new parameter section 426 may allow for a user to adjust one or more parameters. Updating of one or more of the parameters may trigger the analysis of the new parameter set by the machine learning model. Changes made to the parameters may generate changes to the predicted entrainment response section 427. The predicted response visualization may be updated based on receiving of an updated results from the machine learning model.

Figure 5:
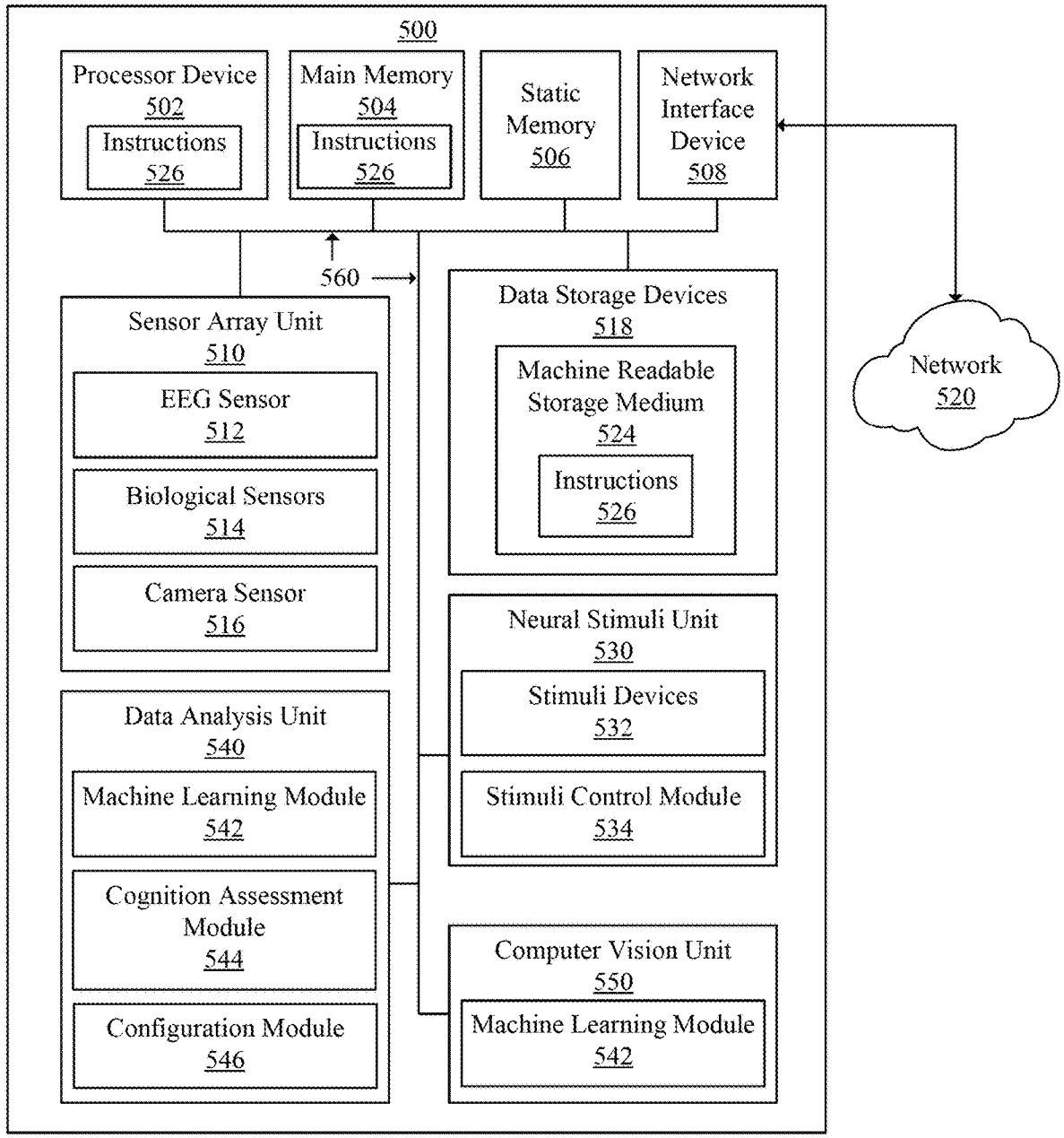
FIG. 5 is a diagram illustrating an exemplary computer/control system that may perform processing in some embodiments and in accordance with aspects of the present disclosure.

FIG. 5 illustrates an example machine of a computer system within which a set of instructions, for causing the machine to perform any one or more of the methodologies discussed herein, may be executed. In alternative implementations, the machine may be connected (e.g., networked) to other machines in a LAN, an intranet, an extranet, an ad-hoc network, a mesh network, and/or the Internet. The machine may operate in the capacity of a server or a client machine in client-server network environment, as a peer machine in a peer-to-peer (or distributed) network environment, or as a server or a client machine in a cloud computing infrastructure or environment.

The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 500 includes a processing device 502, a main memory 504 (e.g., read-only memory (ROM), flash memory, dynamic random access memory (DRAM) such as synchronous DRAM (SDRAM) or Rambus DRAM (RDRAM), etc.), a static memory 506 (e.g., flash memory, static random access memory (SRAM), etc.), and a data storage device 518, which communicate with each other via a bus 560.

Processing device 502 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 502 may also be one or more special-purpose processing devices such as an application specific integrated circuit (ASIC), a field programmable gate array (FPGA), a digital signal processor (DSP), network processor, or the like. The processing device 502 is configured to execute instructions 526 for performing the operations and steps discussed herein.

The computer system 500 may further include a network interface device 408 to communicate over the network 520. The computer system 500 also may include sensor array unit 510. Sensor array unit 510 may comprise an EEG sensor 512, biological sensors 514 and camera sensor 516.

The data storage device 518 may include a machine-readable storage medium 524 (also known as a computer-readable medium) on which is stored one or more sets of instructions or software 526 embodying any one or more of the methodologies or functions described herein. The instructions 526 may also reside, completely or at least partially, within the main memory 504 and/or within the processing device 502 during execution thereof by the computer system 500, the main memory 504 and the processing device 502 also constituting machine-readable storage media. Information, including data used in the processes and methods of the system and the one or more sets of instructions or software, may also be stored in blockchain, as NFTs or other decentralized technologies.

Neural stimuli unit 530 may comprise stimuli devices 532 and stimuli control module 534. Neural stimuli unit 530, stimuli devices 532 and stimuli control module 534 may be the same or similar to that of the neural stimuli unit 205, stimuli devices 206 and stimuli control module 207 disclosed in FIG. 2A.

Data analysis unit 540 may comprise machine learning module 542, cognition assessment module 544 and configuration module 546. Data analysis unit 540, machine learning module 542, cognition assessment module 544 and configuration module 546 may be the same or similar to that of the data analysis unit 215, machine learning module 216, cognition assessment module 217 and configuration module 218 disclosed in FIG. 2A.

Computer vision module 550 may comprise machine learning module 542. The computer vision module 550 may use the machine learning module to analyze captured images of a user and/or the computer system 500. The analysis may be used to identify the computer system 500 and the user as well as determine their position in relation to each other. This determination may then be used to verify a correct placement of the computer system. If the placement is not correct, the analysis may be used in directing the user to reposition the computer system so as to correct the placement.

In one implementation, the instructions 526 include instructions to implement functionality corresponding to the components of a device to perform the disclosure herein. While the machine-readable storage medium 524 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

It will be appreciated that the present disclosure may include any one and up to all of the following examples.

Example 1. A neural entrainment platform configured to induce and verify neural entrainment of a user, the platform comprising: a neural entrainment system, wherein the neural entrainment system further comprises: one or more neural stimuli modules, wherein the neural stimuli modules further comprise one or more stimuli devices and one or more stimuli control modules, and wherein the neural stimuli module is configured to: set, by the stimuli control module, one or more operational parameters for the one or more stimuli devices; control, by the stimuli control module, the operation of the one or more stimuli devices, wherein the operation of the one or more stimuli devices is based at least in part on the one or more operational parameters for the one or more stimuli devices; and deliver, by the one or more stimuli devices, one or more neural stimuli to the user; a verification module, wherein the verification module further comprises: one or more sensor modules, wherein, at least one of the sensor modules is configured to receive biological signals from the user; and a data analysis module, wherein the data analysis is configured to: determine, by a cognitive assessment module, one or more efficacy value of a combination of the one or more neural stimuli, wherein the efficacy values are based at least in part on received user input and results from one or more clinical assessments; analyze, by a machine learning module, data received from the one or more sensor modules, wherein the data received includes one or more biological signals, the operational parameters of the one or more stimuli devices and the determined efficacy value; determine, based on the analysis, one or more adjustments to the one or more operational parameters of the one or more stimuli devices; and provide the determined one or more adjustments to the stimuli control module, wherein the stimuli control module applies the one or more adjustments to the one or more stimuli devices.

Example 2. The neural entrainment platform of Example 1, wherein the verification module further comprises a camera module configured to: capture images of the user wearing the neural entrainment system; and determine, by a configuration module, proper placement of the neural entrainment system, wherein the determination is based at least in part on the captured images of the user and analysis of the one or more biological signals received by the one or more sensor modules.

Example 3. The neural entrainment platform of any one of Examples 1-2, wherein the neural entrainment system is configured to provide the user with adjustment directions to reposition the neural entrainment system to the proper placement.

Example 4. The neural entrainment platform of any one of Examples 1-3, wherein one of the one or more sensor modules is an electroencephalogram (EEG).

Example 5. The neural entrainment platform of any one of Examples 1-4, wherein each of the one or more stimuli devices are configured to deliver neural stimuli in the form of visible light, audible sound, infrared light, ultraviolet light, infrasound, ultrasound, physical vibrations, transcranial direct and alternating current stimulation (tDCS/tACS), transcranial magnetic stimulation (TMS) or aromas.

Example 6. The neural entrainment platform of any one of Examples 1-5, wherein each of the one or more stimuli devices are controlled to deliver neural stimuli based on a stimuli profile, wherein the stimuli profile comprises operational parameters for amplitude, duration, frequency and wave shape.

Example 7. The neural entrainment platform of any one of Examples 1-6, wherein adjustments are made to the stimuli profile of one or more of the stimuli devices when one or more determined efficacy values are below a predetermined threshold.

Example 8. The neural entrainment platform of any one of Examples 1-7, wherein the adjustments are based at least in part on a relationship between two or more neural stimuli and biological signals received in response to the plurality of neural stimuli.

Example 9. The neural entrainment platform of any one of Examples 1-8, wherein the machine learning module is trained on one or more datasets, retrieved from one or more databases, wherein the datasets comprise a plurality of records each comprising one or more stimuli profiles of neural stimuli, one or more biological signals received in response to the neural stimuli, received user input, results from one or more clinical assessments and a determined efficacy value.

Example 10. A computer implemented method for inducing and verifying neural entrainment of a user, the method comprising: controlling, by a stimuli control module, one or more stimuli devices, wherein the controlling comprises: setting one or more operational parameters for the one or more stimuli devices; delivering, by a first stimuli device, a first neural stimuli to the user; delivering, by a second stimuli device, a second neural stimuli to the user; measuring, by one or more sensors, one or more biological signals from the user; analyzing, by a data analysis module, the one or more biological signals; adjusting, based on the analysis of the one or more biological signals, the one or more operational parameters for the first stimuli device and the second stimuli device; and assessing, by a cognitive assessment module, an efficacy value of a combination of the first neural stimuli and the second neural stimuli, wherein the assessed efficacy is based on received user input and results from one or more clinical assessments.

Example 11. The method of Examples 10, wherein one of the one or more sensor modules is an electroencephalogram (EEG).

Example 12. The method of any one of Examples 10-11, wherein each of the one or more stimuli devices are configured to deliver neural stimuli in the form of visible light, audible sound, infrared light, ultraviolet light, infrasound, ultrasound, physical vibrations, transcranial direct and alternating current stimulation (tDCS/tACS), transcranial magnetic stimulation (TMS) or aromas.

Example 13. The method of any one of Examples 10-12, wherein each of the one or more stimuli devices are controlled to deliver neural stimuli based on a stimuli profile, wherein the stimuli profile comprises operational parameters for amplitude, duration, frequency and wave shape.

Example 14. The method of any one of Examples 10-13, wherein adjustments are made to the stimuli profile of one or more of the stimuli devices when the assessed efficacy value is below a predetermined threshold.

Example 15. The method of any one of Examples 10-14, wherein the adjustments are based at least in part on a relationship between two or more neural stimuli and biological signals received in response to the plurality of neural stimuli.

Example 16. The method of any one of Examples 10-15, wherein each of the one or more stimuli devices are controlled to deliver neural stimuli based on a stimuli profile, wherein the stimuli profile comprises operational parameters for amplitude, duration, frequency and wave shape.

Example 17. The method of any one of Examples 10-16, wherein adjustments are made to the stimuli profile of one or more of the stimuli devices when the determined efficacy value is below a predetermined threshold.

Example 18. The method of any one of Examples 10-17, wherein the adjustments are based at least in part on a relationship between two or more neural stimuli and biological signals received in response to the plurality of neural stimuli.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

Various general purpose systems may be used with programs in accordance with the teachings herein, or it may prove convenient to construct a more specialized apparatus to perform the method. The structure for a variety of these systems will appear as set forth in the description above. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A neural entrainment platform configured to induce and verify neural entrainment of a user, the platform comprising:
a neural entrainment system, wherein the neural entrainment system further comprises:
one or more neural stimuli modules, wherein each neural stimuli module of the one or more neural stimuli modules further comprises one or more stimuli devices and a stimuli control module, and wherein each neural stimuli module of the one or more neural stimuli modules is configured to:
set, by the stimuli control module, one or more operational parameters for the one or more stimuli devices;
control, by the stimuli control module, an operation of the one or more stimuli devices, wherein the operation of the one or more stimuli devices is based at least in part on the one or more operational parameters for the one or more stimuli devices; and
deliver, by the one or more stimuli devices, one or more neural stimuli to the user; and
a verification module, wherein the verification module further comprises:
one or more sensor modules, wherein, at least one of the one or more sensor modules is configured to receive one or more biological signals from the user; and
a data analysis module configured to:
determine, by a cognitive assessment module, one or more efficacy values value of a combination of the one or more neural stimuli, wherein the one or more efficacy values are based at least in part on received user input and results from one or more clinical assessments;
analyze, by a machine learning model generated by a machine learning module, data received from the one or more sensor modules, wherein the data received includes the one or more biological signals, the one or more operational parameters of the one or more stimuli devices and the one or more determined efficacy values, and wherein the machine learning model is trained on one or more training datasets that are retrieved from one or more databases, wherein each training dataset of the one or more training datasets comprises a plurality of training records each comprising one or more historic stimuli profiles of historic neural stimuli, one or more historic biological signals received in response to the historic neural stimuli, historic received user input, historic results from the one or more clinical assessments and one or more historic determined efficacy values;
determine, based on the analysis, one or more adjustments to the one or more operational parameters of the one or more stimuli devices; and
provide the determined one or more adjustments to the stimuli control module, wherein the stimuli control module applies the one or more adjustments to the one or more stimuli devices.

2. The neural entrainment platform of claim 1, wherein the verification module further comprises a camera module configured to:
capture images of the user when said user wears the neural entrainment system; and
determine, by a configuration module, proper placement of the neural entrainment system, wherein the proper placement determination is based at least in part on the captured images of the user and the analysis of the one or more biological signals received by the one or more sensor modules.

3. The neural entrainment platform of claim 2, wherein the neural entrainment system is configured to provide the user with adjustment directions to reposition the neural entrainment system to the proper placement.

4. The neural entrainment platform of claim 1, wherein one of the one or more sensor modules is an electroencephalogram (EEG).

5. The neural entrainment platform of claim 1, wherein each of the one or more stimuli devices are configured to deliver a neural stimuli selected from:
visible light, audible sound, infrared light, ultraviolet light, infrasound, ultrasound, physical vibrations, transcranial direct and alternating current stimulation (tDCS/tACS), transcranial magnetic stimulation (TMS) or aromas.

6. The neural entrainment platform of claim 5, wherein each of the one or more stimuli devices are controlled to deliver neural stimuli based on a stimuli profile, wherein the stimuli profile comprises an operational parameter for amplitude, duration, frequency and wave shape.

7. The neural entrainment platform of claim 6, wherein adjustments are made to the stimuli profile of one or more of the one or more stimuli devices when the determined efficacy value is not within a first window of values.

8. The neural entrainment platform of claim 7, wherein the adjustments are based at least in part on a relationship between a subset of the one or more neural stimuli and the one or more biological signals received in response to each neural stimuli of the subset.

9. The neural entrainment platform of claim 6, wherein the data analysis module is further configured to generate one or more predicted efficacy values and one or more predicted biological signals based at least in part on an analysis of the determined one or more adjustments to the one or more operational parameters of the one or more stimuli devices.

10. The neural entrainment platform of claim 9, wherein one or more new stimuli profiles are generated based at least in part on the one or more predicted efficacy values and the one or more predicted biological signals.

11. A computer implemented method for inducing and verifying neural entrainment of a user, the method comprising:
controlling, by a stimuli control module, one or more stimuli devices, wherein the controlling comprises:
setting one or more operational parameters for the one or more stimuli devices;
delivering, by a first stimuli device of the one or more stimuli devices, a first neural stimuli to the user;
delivering, by a second stimuli device of the one or more stimuli devices, a second neural stimuli to the user;
measuring, by one or more sensors, one or more biological signals from the user;
analyzing, by a machine learning model generated by a machine learning module operating on a data analysis module, the one or more biological signals;
adjusting, based on the analysis of the one or more biological signals, the one or more operational parameters for the first stimuli device and the second stimuli device;

administering one or more clinical assessments to the user;

receiving, from the user, answers to the one or more clinical assessments;

generating a result for each of the one or more clinical assessments based on the received answers;

assessing, by a cognitive assessment module, an assessed efficacy value of a combination of the first neural stimuli and the second neural stimuli, wherein the assessed efficacy value is based on the generated results for the one or more clinical assessments; and training, by the machine learning module, the machine learning model on one or more training datasets that are retrieved from one or more databases, wherein each training dataset of the one or more training datasets comprises a plurality of training records each comprising one or more historic stimuli profiles of historic neural stimuli, one or more historic biological signals received in response to the historic neural stimuli, historic received user input, historic results from the one or more clinical assessments and one or more historic determined efficacy values.

12. The method of claim 11, wherein one of the one or more sensors is an electroencephalogram (EEG).

13. The method of claim 12, wherein the first stimuli device and the second stimuli device are configured to deliver a neural stimuli selected from:

visible light, audible sound, infrared light, ultraviolet light, infrasound, ultrasound, physical vibrations, transcranial direct and alternating current stimulation (tDCS/tACS), transcranial magnetic stimulation (TMS) or aromas.

14. The method of claim 13, wherein the first stimuli device and the second stimuli device are controlled to deliver neural stimuli based on a stimuli profile, wherein the stimuli profile comprises an operational parameter for amplitude, duration, frequency and wave shape.

15. The method of claim 14, wherein adjustments are made to the stimuli profile of the first stimuli device and the second stimuli device based at least in part on the assessed efficacy value and a correspondence between the assessed efficacy value and a first window of values.

16. The method of claim 15, wherein the adjustments are based at least in part on a relationship between the first neural stimuli, the second neural stimuli and biological signals received in response to the first neural stimuli and the second neural stimuli.

* * * * *